(12) United States Patent
Weijand et al.

(10) Patent No.: US 10,974,052 B2
(45) Date of Patent: Apr. 13, 2021

(54) MEDICAL COMMUNICATION AND POWER CHARGING SYSTEM

(71) Applicant: ONWARD MEDICAL B.V., Eindhoven (NL)

(72) Inventors: Koen Weijand, l'Alfàs del Pi (ES); Hans W. Pflug, Waalre (NL)

(73) Assignee: ONWARD MEDICAL B.V., Eindoven (NL)

(*) Notice: Subject to any disclaimer, the term of this patent is extended or adjusted under 35 U.S.C. 154(b) by 0 days.

(21) Appl. No.: 16/190,833

(22) Filed: Nov. 14, 2018

(65) Prior Publication Data
US 2019/0143128 A1   May 16, 2019

(30) Foreign Application Priority Data
Nov. 15, 2017   (EP) ..................... 17201800

(51) Int. Cl.
| | |
|---|---|
| *A61N 1/372* | (2006.01) |
| *H04Q 9/00* | (2006.01) |
| *H01Q 1/27* | (2006.01) |
| *A61N 1/378* | (2006.01) |
| *H01Q 5/50* | (2015.01) |

(52) U.S. Cl.
CPC ....... *A61N 1/37229* (2013.01); *A61N 1/3787* (2013.01); *A61N 1/37223* (2013.01); *H01Q 1/273* (2013.01); *H01Q 5/50* (2015.01); *H04Q 9/00* (2013.01); *H04Q 2209/883* (2013.01)

(58) Field of Classification Search
None
See application file for complete search history.

(56) References Cited

U.S. PATENT DOCUMENTS

| | | | | |
|---|---|---|---|---|
| 4,303,904 | A * | 12/1981 | Chasek ..................... | G07F 7/02 235/384 |
| 5,948,004 | A * | 9/1999 | Weijand ................... | H02M 3/07 607/72 |
| 8,265,770 | B2 | 9/2012 | Toy et al. | |
| 8,630,717 | B2 | 1/2014 | Olson et al. | |
| 9,520,887 | B1 * | 12/2016 | Zhuang ................. | H03L 7/1072 |
| 2004/0087286 | A1 * | 5/2004 | Inoue ...................... | H04B 1/52 455/130 |
| 2005/0075693 | A1 * | 4/2005 | Toy ..................... | A61N 1/37223 607/60 |
| 2006/0142822 | A1 | 6/2006 | Tulgar | |

(Continued)

*Primary Examiner* — Fekadeselassie Girma (57) ABSTRACT

The present disclosure relates to a communication and powering system, such as a medical communication and powering system. An example communication and powering system includes at least one communication module with a communication transmitter, which is configured and arranged to transmit and send communication signals, at least one charging and/or powering module with an energy charging and/or powering transmitter, which is configured and arranged to provide and/or transmit charging and/or powering energy, and at least one receiver being a receiver for communication signals and energy, wherein the receiver has and/or can be switched into a first status for receiving communication signals provided by the communication module and wherein the receiver has and/or can be switched into a second status for receiving energy provided by the charging and/or powering module.

20 Claims, 4 Drawing Sheets

(56) References Cited

U.S. PATENT DOCUMENTS

| | | | | |
|---|---|---|---|---|
| 2010/0279606 | A1* | 11/2010 | Hillan | H04B 5/00 |
| | | | | 455/41.1 |
| 2010/0298910 | A1* | 11/2010 | Carbunaru | A61N 1/3605 |
| | | | | 607/60 |
| 2011/0112611 | A1* | 5/2011 | Aghassian | A61N 1/37229 |
| | | | | 607/60 |
| 2012/0161531 | A1* | 6/2012 | Kim | H02J 50/80 |
| | | | | 307/104 |
| 2012/0161721 | A1* | 6/2012 | Neethimanickam | H02J 50/20 |
| | | | | 320/167 |
| 2014/0339909 | A1* | 11/2014 | Sugawara | H02J 7/025 |
| | | | | 307/104 |
| 2015/0012061 | A1 | 1/2015 | Chen | |
| 2015/0022143 | A1* | 1/2015 | Kim | H02J 9/005 |
| | | | | 320/108 |
| 2015/0126120 | A1* | 5/2015 | Chen | H04B 1/0057 |
| | | | | 455/41.2 |
| 2015/0188592 | A1* | 7/2015 | Solondz | H04B 1/18 |
| | | | | 455/501 |
| 2015/0200561 | A1* | 7/2015 | Lee | H02J 7/0042 |
| | | | | 320/108 |
| 2016/0197488 | A1* | 7/2016 | Hada | H02J 5/005 |
| | | | | 307/104 |
| 2017/0098951 | A1* | 4/2017 | Olgun | H02J 50/12 |
| 2017/0338570 | A1* | 11/2017 | Myers | H04B 1/00 |
| 2018/0294547 | A1* | 10/2018 | Park | H04B 7/0802 |
| 2019/0033622 | A1* | 1/2019 | Olgun | H02J 7/025 |

* cited by examiner

MEDICAL COMMUNICATION AND POWER CHARGING SYSTEM

CROSS REFERENCE TO RELATED APPLICATION

The present application claims priority to European Patent Application No. 17201800.4 entitled "A medical communication and power charging system," filed on Nov. 15, 2017. The entire contents of the above-listed application are hereby incorporated by reference in their entirety for all purposes.

TECHNICAL FIELD

The present disclosure relates to a communication and powering system, which may include a medical communication and powering system.

BACKGROUND AND SUMMARY

Communication and power charging system in a medical field may be used to submit energy and communication signals transcutaneously.

For example US 2015/0012061 A1 relates to a medical device for providing a stimulation therapy including a call configurator to receive both inductive charging and telemetric signals. Inductive charging signals are in a first frequency band. The telemetric signals are in a second frequency band higher than the first frequency band. The medical device includes inductive charging circuitry configured to provide electrical power to the medical device via the inductive charging signals. The medical device includes telemetric circuitry configured to conduct telecommunications with the external device via the telemetric signals. The medical device includes a first component electrically coupled between the coil and the inductive charging circuitry. The first component is configured to allow the inductive charging signals to pass through. The medical device includes a second component electrically coupled between the coil and the telemetric circuitry. The second component is configured to substantially drop the inductive charging signals while allowing telemetric signals to pass through.

Alternative solutions are for example disclosed by EP 1 680 182 A1, EP 1 675 648 A1 and EP 1 575 665 A1.

It is an object of the present disclosure to combine communication and wireless-charging within one electronic circuit, such as for a medical device. In this way, the electronic circuit may be simplified and is easier in handling.

This object is solved according to the present disclosure with a system with at least one communication module with a communication transmitter which is configured and arranged to transmit and send communication signals; at least one charging and/or powering module with an energy charging and/or energy transferring transmitter which is configured and arranged to provide and/or transmit charging and/or powering energy; and at least one receiver for communication signals and energy, wherein the receiver has and/or is configured to be switched into a first status for receiving communication signals provided by the communication module and wherein the receiver has and/or is configured to be switched into a second status for receiving energy provided by the charging module. Accordingly, a communication and powering system, e.g., power/energy transfer/charging system, such as a medical communication and power/energy transfer/charging system is provided, comprising: at least one communication module with a communication transmitter, which is configured and arranged to transmit and send communication signals, at least one charging and/or powering/energy transferring module with an energy charging and/or powering/energy transferring transmitter, which is configured and arranged to provide and/or transmit charging and/or powering energy, at least one receiver being a receiver for communication signals and charging power/energy, wherein the receiver has and/or can be switched into a first status for receiving communication signals provided by the communication module and wherein the receiver has and/or can be switched into a second status for receiving charging energy provided by the charging module.

The disclosed systems and methods are based on the basic principle that there is one communication transmitter and one energy charging and/or powering/energy transferring transmitter, which communicate with the same receiver. With the communication transmitter communication signals of any kind may be transmitted. With the energy charging and/or powering/energy transferring transmitter, energy may be transferred from the transmitter via the receiver to a power and/or energy source like a battery or even more simple, just to provide energy more or less online. By this, fewer elements for the whole communication and power charging systems are needed and the function of receiving communication signals and charging energy by one common receiver allows easier and simpler design of electronics on the receiving side. For example, in medical cases at least the receiver is implanted. If the receiver comprises only a low number of elements than the construction of the circuit is less power consuming and more reliable.

By providing power/energy "online," power/energy may also be supplied to an implanted device to enable communications so the implanted device can report any issues associated with the implanted device and in some examples even to initiate a recovery procedure. Accordingly, with the charging and/or powering/energy transferring module, power/energy can be supplied, and with the communication module and the receiver, signals can be exchanged, also vice versa. Then, the receiver may not only receive, but also send and transmit signals back to the communication module and thus work as a transceiver.

It is possible that the first status and the second status are enabled at the same time. In such a way of operation concurrent communication signal and charging energy transmission may be provided.

Alternatively, it is possible that the first status and the second status are alternating and/or not enabled at the same time. By this, it is possible to have a well-defined transmission of communication signals followed by transmission of charging energy and vice versa.

Moreover, it is possible that the communication transmitter is configured and arranged to transmit and send communication signals within a first frequency range and that the energy charging transmitter is configured and arranged to provide and/or transmit charging energy within a second frequency range, wherein the first and second frequency range are different from each other. By using different frequency ranges for the communication signals and for the charging energy it is possible to have only one receiver on the receiving side. This helps to simplify the circuit design and the electronic design on the receiving side.

The communication transmitter may be also embodied as transceiver, e.g., a combined module, which has transmitting capabilities and receiving capabilities. This way, the communication transmitter is then a transmitter and a receiver.

Furthermore, it is possible that the receiver is implantable or implanted into a subject and the communication module and/or the charging and/or powering/energy transferring module are not implanted into a subject. Generally it is possible that the communication module and/or the communication transmitter may be implanted as well. In general, the disclosed systems and/or methods may include or be configured to provide, at least partially, a transcutaneous transmission of communication signals from outside of the body to the inside of the body and vice versa. The disclosed systems and/or methods may also include or be configured to provide a transmission of charging energy transcutaneously at least from the outside of the body to the inside of the body. In other words, the system has parts that are arranged externally and outside of the human body and parts of the system that are arranged within, that is, implanted into the human body.

Moreover, at least one of the communication transmitter and the energy charging and/or powering/energy transferring transmitter may be embodied as an antenna or antenna coil. By this, for example magnetic induction may be used and transmitted by the antenna or antenna coil. For example, one antenna or antenna coil may be included in or provided for the communication module and another, second antenna or antenna coil may be included in or provided for the charging module.

Furthermore, the receiver may comprise an antenna, such as an antenna coil, and a communication and a charging diplexer (hereinafter also diplexer or C/C-diplexer). With the antenna, communication signals and energy may be received. The diplexer may enable frequency-domain multiplexing to be performed. These joint frequency bands may be occupied by two parts of the diplexer. Accordingly, signals with different frequencies can coexist without interfering with each other. By this, the design of the receiver can be simplified as only a single antenna for the receiver may be used. No further antenna is needed. Generally speaking, a further antenna may be used for redundancy reasons. However, such a further antenna or further antennas are no longer necessary, as a single antenna is sufficient.

The antenna may be an inductor and the diplexer may comprise a switch to ground or reference, at least one capacitor, such as a first capacitor and a second capacitor, connected to the antenna, wherein the antenna and the second capacitors form a resonant tank. Such a tank circuit may be also called LC-circuit or resonant circuit and may be an electric circuit consisting of a conductor, and a capacitor, which are connected together. The circuit can act as an electrical resonator, an electrical analogue of a tuning fork, storing energy oscillating at the circuit resonance frequency. LC circuits are used either for generating signals at the particular frequency or picking out a signal at the particular frequency from a more complex signal. This function may be called bandpass filter. By such a tank circuit it is possible to receive charging energy and communication signals very easily and reliably. Moreover, all components may be formed by passive electronic components. No battery is needed for the receiver. The basic idea of this concept may be described as follows:

In principle there maybe for example at least three capacitors and at least one inductor/antenna and at least one switch:
  one capacitor in parallel to a communication port, which can be hidden inside a communication chip;
  two capacitors in series between the communication port and the inductor; and
  a switch across the communication (com) port.

When the switch is open in this example, then the inductor resonates with the parallel capacitance of the com port, and this capacitance is dominantly determining the resonance frequency, with little influence of the series capacitors.

When the switch is closed in this example, then the resonance is determined by the net capacitance of the two series connected capacitors and the inductance. The series capacitors are now parallel resonating capacitors.

In this example, the purpose of the switch is two-fold: on the one side the switch is protecting the com port input against too high voltages and creates a lower resonance frequency path using the two series capacitors. On the other side, the two series capacitors are forming a voltage divider when the switch is closed and the associated ratio can be adapted to a required impedance matching to the subsequent rectifier.

For example, in the connection between the first capacitor and the second capacitor a branch-off line is connected, wherein the branch-off line is connected to a connection point, the connection point being connection to a charging line and a communication line, wherein in the communication line a third capacitor and a connection to a switch to ground or reference is arranged. This specific arrangement allows a very easy passive arrangement of electronic components forming the resonant tank/LC-circuit. Also only a very low number of electronic components may be used.

Moreover, it is possible that the third capacitor is arranged between the connection point and the connection to the switch to ground.

Additionally, it is possible that in the connection line connecting the second capacitor and the antenna a connection to ground or reference is provided. By this alternative an additional embodiment may be realized.

It is also possible that from the antenna a branch-off line is connected, wherein the branch-off line is connected to a connection point, the connection point being in connection to a charging line and a communication line, wherein in the communication line a capacitor and a connection to a switch to ground is arranged. Again, only a single antenna at the receiving side may be used.

Additionally, the capacitor may be arranged between the connection point and the connection to the switch to ground.

Also, it is possible that the antenna may be connected to a circuit with a capacitor and connection to ground, wherein the capacitor and the connection to ground are arranged in series. In this embodiment still only one antenna on the receiving side may be used, like a deep whole antenna. The individual elements will not act as a similar antenna on the same frequency.

Moreover, the receiver may be connected to a separate implantable medical device (IMD).

For example, the implantable medical device may be an implantable pulse generator (IPG).

By separating the implantable medical from the system of the communication and power charging system specific advantage may be achieved.

For example, the communication and charging and/or powering system may be well defined and include only very few passive components. Also, no complete revision of an already implanted and existing implantable medical device is needed. So, the charging and communication system may be added to existing implanted medical devices. By separating the IMD with the system, it is also possible to design a platform independent communication and charging system, which is not directly and necessarily linked to the implantable medical device. The range of use is thereby increased.

The implantable medical device (IMD) may be rechargeable or powered (online) via the receiver by means of the charging module and, via the receiver, communication signals may be exchanged between the implantable medical device (IMD) and the communication module. By this recharging and the exchange of communication signals, e.g., for telemetry, monitoring or re-programming of the IMD may be exchanged and transmitted.

BRIEF DESCRIPTION OF THE DRAWINGS

Further details and advantages of the present disclosure shall now be disclosed in connection with the drawings.

It is shown in.

DETAILED DESCRIPTION

Figure 1:
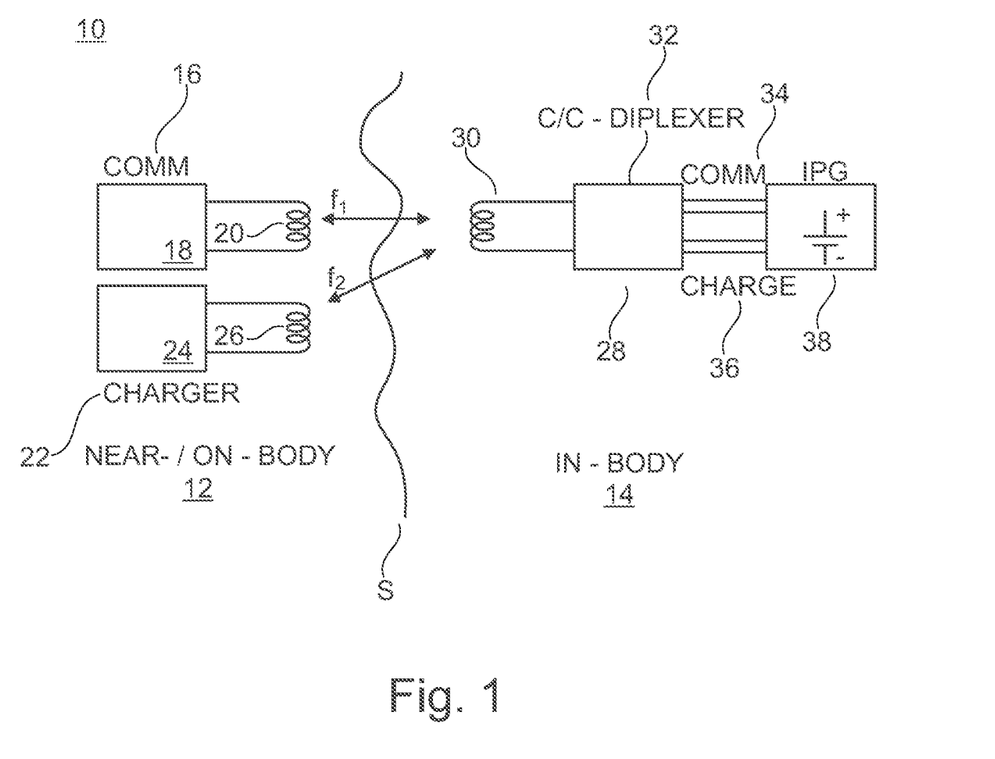
FIG. 1 a schematic drawing of a communication and powering system in a first example according to the present disclosure.

FIG. 1 shows a communication and powering system 10 in a first example embodiment according to the present disclosure.

The communication and powering system 10 comprises an external body part 12 and an implanted in-body part 14.

The external body part 12 is near-/on-body and for example embodied as wearable.

The external body part 12 comprises at least one communication module 16, comprising a communication electronics 18 and an antenna coil 20.

The communication module 16 is a communication module 16 with a communication transmitter, here the antenna coil 20, which is configured in a range to transmit and send communication signals.

It is possible that the communication module 16 is not only acting as a transmitter, but also as a receiver and thus forms a transceiver.

Furthermore, the external part 12 also comprises a charging and/or powering/energy transferring module 22 comprising a charger 24 and an energy charging and/or powering/energy transferring transmitter 26.

The energy charging and/or powering/energy transferring transmitter 26 is also embodied as an antenna coil 26.

The skin barrier of the patient is also shown in FIG. 1 and denoted with reference sign S.

In the shown embodiment in FIG. 1, the communication and powering system 10 is a medical communication and powering system 10 for transcutaneously transmitting communication signals and also for transmitting energy and/or power for charging the energy source of an implantable medical device (IMD).

Also, this way power/energy may be supplied online (when there is no communication, e.g., no communication signals are exchanged).

The in-body part 14 comprises a receiver 28.

The receiver 28 is a receiver 28 for communication signals and (charging) power/energy.

The receiver 28 comprises an antenna/coil 30, a C/C-diplexer 32 (e.g., communication and charging diplexer 32), a communication line COMM 34 and a charging line CHARGE 36.

The communication line COMM 34 and the charging line CHARGE 36 are connected to an implantable medical device (IMD) 38, here an implantable pulse generator (IPG) 38.

Figure 2:
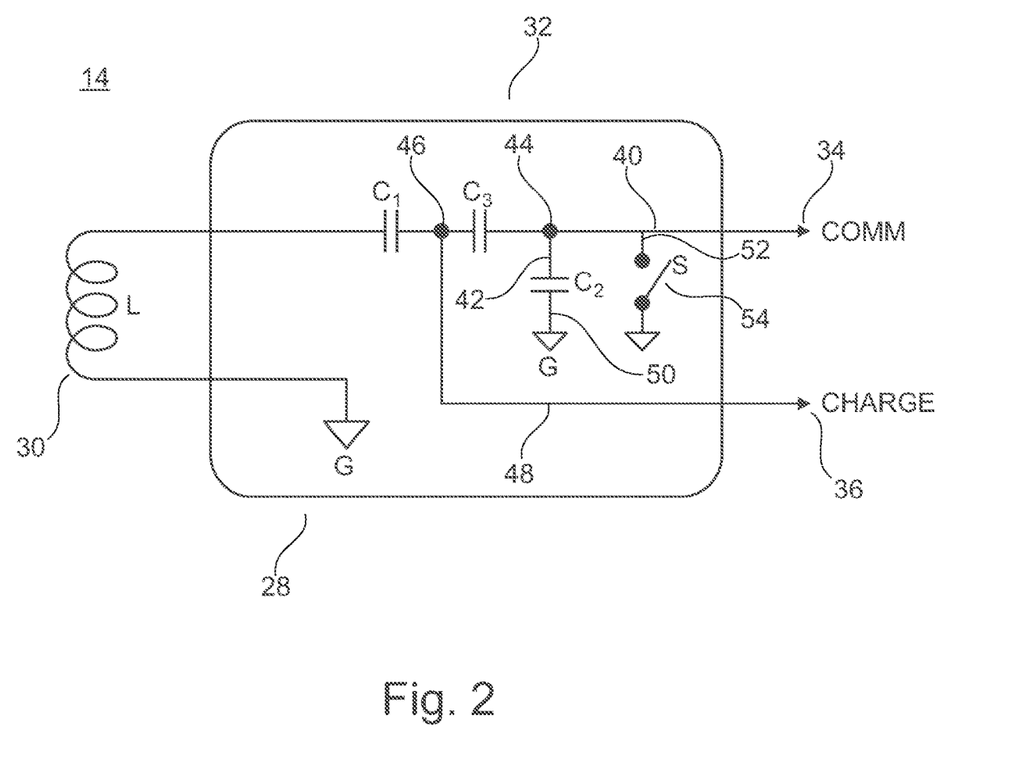
FIG. 2 a detail of the C/C-diplexer circuit according to the example of FIG. 1.

FIG. 2 shows further details of the C/C-diplexer 32.

The C/C-diplexer 32 has a C/C-diplexer circuit comprising the antenna coil 30, which acts as an inductor L.

The inductor L is connected on one side to ground G and on its other end to a first capacitor C1. Following this route there is a further line coming from the capacitor C1 to the communication line COMM 34, which is denoted with reference number 40.

Within this line 40 there is a capacitor C2 and a capacitor C3.

The capacitor C2 is arranged in a branch-off line 42, which is connected to line 40 at the connection point 44.

The capacitor C3 is in line 40, in between the connection point 44 and the capacitor C1.

Between capacitor C1 and capacitor C3 there is another connection point 46, from which a branch-off line to the charging line CHARGE 36 is connected. This branch-off line is, as long as it is arranged within the C/C-diplexer circuit 32, denoted with reference number 48.

After capacitor C2, there is a line to the ground G, which is denoted with reference number 50.

In line 40 and between communication line 34 and the connection point 44, there is another branch-off line 52.

In this branch-off line 52, there is a switch 54 arranged, which also leads to ground G, if switch 54 is closed.

The functionality of the C/C-diplexer circuit 32 of FIG. 2 and also of the system 10 may be described as follows:

In FIG. 2, L represents the inductor of the receiver 28.

This inductor L forms, together with capacitor C2 a resonant tank or a so-called LC-circuit.

The capacitor C2 is the dominant capacitor determining the resonance frequency, while the capacitors C1 and C3 act as coupling capacitors, not strongly determining the resonance frequency.

For communication, the switch (S) 54 will be open.

Capacitor C3 forms a connection to the communication part (COMM), e.g., the communication line 34, of the system in the IPG 38.

L/C2 resonate at frequency range f1 or a specific frequency selected from this first frequency range, see also FIG. 1.

As the signal levels are small during communication, the connected rectifier circuit to the charge output will not reach its functional state. Therefore, the circuit will have a high input impedance.

During charging/powering, the switch (S) 54 is closed and connects capacitor C3 to ground G. This results in no signal at the communication (COMM) port 34. Capacitor C3 is now placed in series to capacitor C1, resulting in a lower resonance frequency range f2 (cf. FIG. 1) of the L/C1/C3 resonant tank or a specific frequency selected from this second frequency range.

The first frequency range f1 and the second frequency range f2 are different from each other.

The output signal is applied to the CHARGE output 36, connected to a rectifying circuit, which is used to charge a rechargeable battery. The capacitor C1 and C3 form a capacitive divider intended to create low impedance source for the rectifier circuit.

Therefore, C3 has a large value compared to C2 and has little influence on the resonance when used as a serious element.

A specific advantage of the system is the usage of a single antenna/coil 30, which acts as an inductor L, which uses design and construction of that part of the system. The system of FIG. 1 and FIG. 2 is described in an asymmetric, un-balanced form. The actual implementation can also be made in a symmetric, balanced form, showing equal functionality.

Generally, it is possible that the first status and the second status of the system are enabled at the same time (not done in the shown embodiment of FIGS. 1 and 2).

Here, the receiver 28 is a receiver 28 for communication signals and (charging) power/energy, wherein the receiver 28 has and/or can be switched into a first status for receiving communication signals provided by the communication module 16 and wherein the receiver 28 has and/or can be switched into a second status for receiving charging energy provided by the charging module 22 the first status and the second status are alternating and/or are not enabled at the same time.

The communication transmitter 20 is configured and arranged to transmit and send communication signals within a first frequency range f1 and the energy charging transmitter 30 is configured and arranged to transmit and send charging energy within a second frequency range f2, the first and second frequency f1, f2 range being different from each other.

Figure 3:
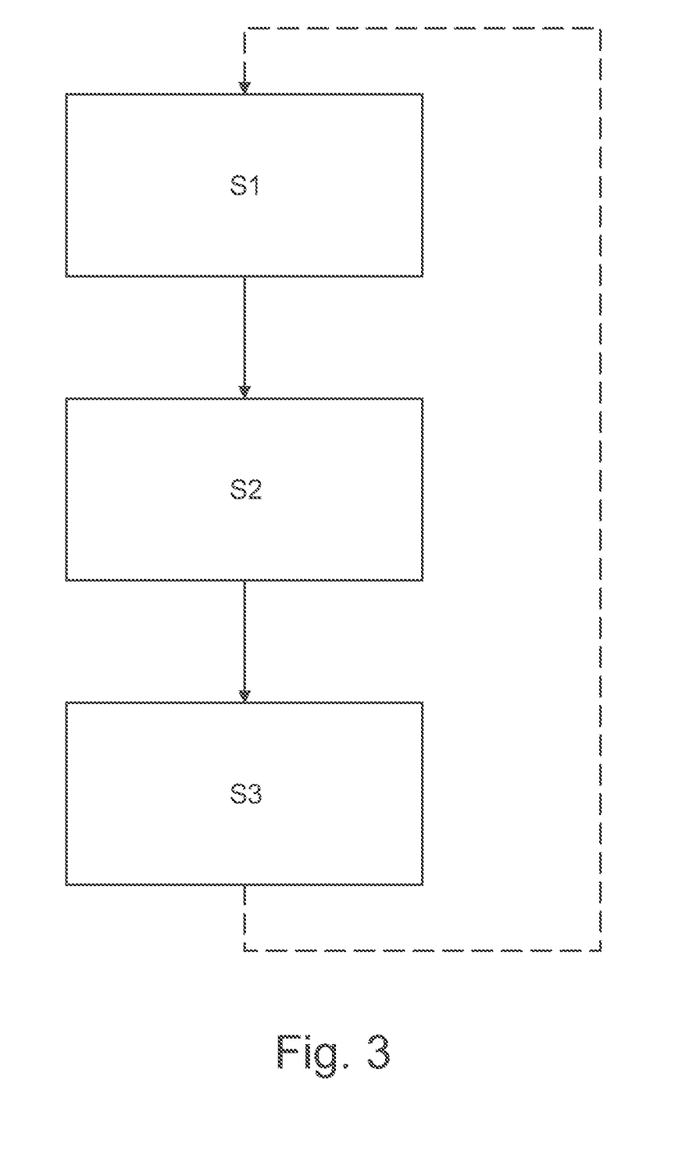
FIG. 3 a flow chart of an example operation of the system of FIG. 1.

FIG. 3 shows a flow chart of the communication and charging/powering procedure conducted with the example of the system 10 according to FIG. 1 and FIG. 2.

In the first step S1 the switch (S) 54 is opened and via the communication module 16 at the frequency f1 communication signals are transcutaneously transmitted to the antenna coil 30 of the in-body part 14. Via the inductor L and lines 40 and 34 the communication signals are transferred to the communication line COMM 34 and may be used to program or re-program the IPG 38.

The communication exchange may be vice versa in this state from the external body part 12 to the internal body part 14.

For example, by using a clock signal, specific periods for transmitting signals into the body and also for receiving signals out of the body may be defined.

In second step S2 then the switch (S) 54 may be closed and so capacitor C3 may be connected to ground G.

Then in the third step S3 energy may be transmitted via the charging and/or powering/energy transferring module 22 and the antenna coil 26 at the frequency F2 to the antenna coil 30 and then transmitted via line 48 to the charge line 36 for charging the battery of the IPG 38.

Steps S1 to S3 may be repeated, continuously follow each other or may be arranged periodically, on demand or the like.

Figure 4:
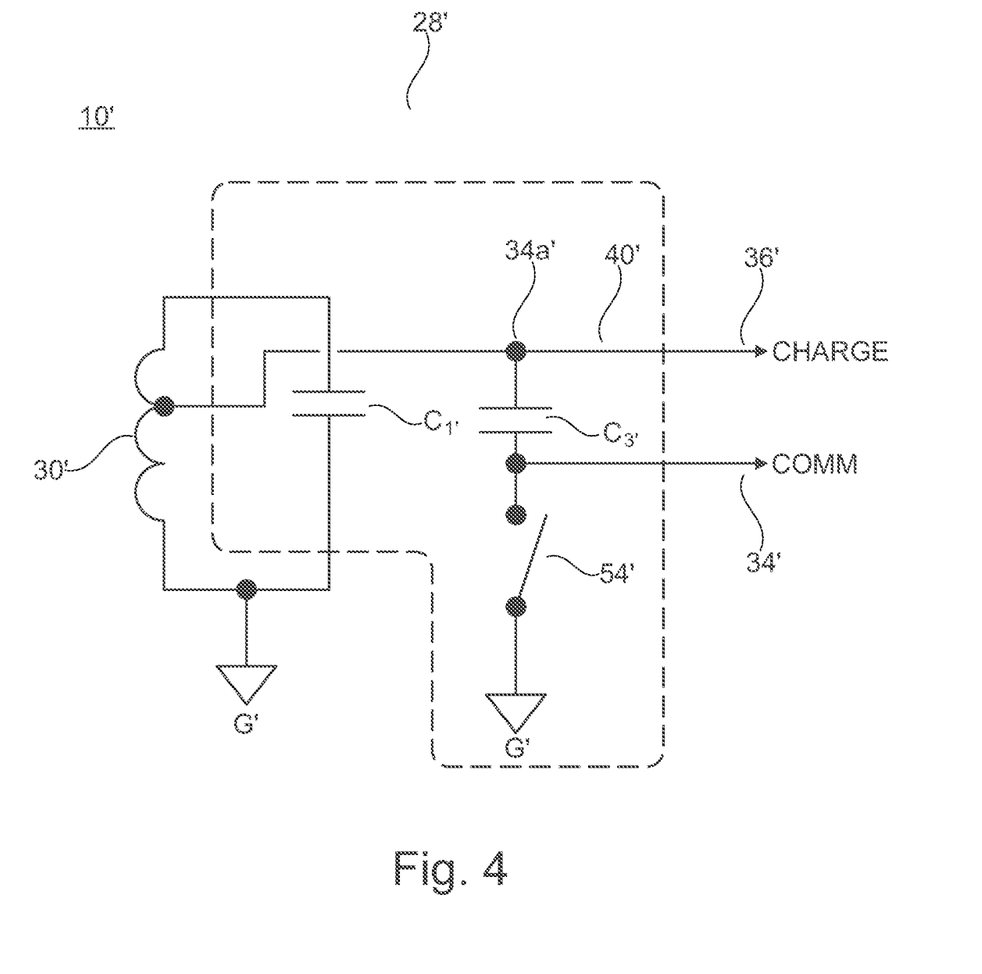
FIG. 4 another example of a communication and powering system according to the present disclosure.

FIG. 4 shows another example of a communication and powering system 10' in a second example embodiment according to the present disclosure.

The system 10' comprises the same structural and functional features as the system 10 described above and shown in FIG. 1-3. However, there are some differences, which shall be described and explained below:

The system 10' also comprises a receiver 28' a C/C-diplexer 32'.

Here, also an inductor coil 30' is present.

The inductor coil 30' is connected to a first capacitor C1'.

Furthermore, there is a branch-off line 40', which is connected to the CHARGE port and charge line 36'.

The branch-off line 40' is directly connected to a winding of the antenna coil 30'.

Moreover, in a connection line to the capacitor C1' a line to ground G' is arranged.

The branch-off line 40' is connected to a connection point 34a', wherein the connection point 34a' is in connection to the charging line 36' and a communication line 34', wherein in the communication line 34' a capacitor C3' and a connection to a switch to ground G' with a switch (S) 54' is arranged.

The antenna 30' is connected to a circuit with a capacitor and a connection to ground G', wherein the capacitor and the connection to ground G' are arranged in series.

The functionality of the embodiment shown in FIG. 4 is equivalent to the one shown in FIG. 1, FIG. 2, and FIG. 3.

This circuit serves for the same purposes shown and described in FIG. 2, by using an inductive impedance transmission instead of a capacitive one.

Note that the example control and functional routines included herein can be used with various communication and power charging system configurations, such as in the medical field. The control methods and routines disclosed herein may be stored as executable instructions in non-transitory memory and may be carried out by the control unit in combination with a medical device, such as an implanted medical device and/or various sensors, actuators, and other system hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations, and/or functions may be repeatedly performed depending on the particular strategy being used. Further, the described actions, operations, and/or functions may graphically represent code to be programmed into non-transitory memory of the computer readable storage medium in the control unit, where the described actions are carried out by executing the instructions in a system including the various hardware components in combination with the electronic control unit.

REFERENCES 10 system
12 external body part
14 implanted in-body part
16 communication module
18 communication electronics
20 antenna coil
22 charging and/or powering/energy transferring module
24 charger
26 energy charging and/or powering/energy transferring transmitter/antenna coil
28 receiver
30 antenna/coil
32 C/C-diplexer
34 communication line
36 charging line
38 implantable pulse generator (IPG)
40 line
42 line
44 connection point
46 connection point
48 branch-off line 50 line
52 branch-off line
54 switch
C1 capacitor
C2 capacitor
C3 capacitor
f1 frequency range
f2 frequency range
G ground
L inductor
S skin barrier
10' system
28' receiver
30' inductor coil
32' C/C-diplexer
34' communication line
34a' connection point
36' Charge port and Charge line
40' branch-off line
54' switch
C1' capacitor
C3' capacitor
G' ground

The invention claimed is:

1. A communication and powering system comprising:
   at least one communication module with a communication transmitter, which is configured and arranged to transmit and send communication signals;
   at least one charging and/or powering module with an energy charging and/or energy transferring transmitter, which is configured and arranged to provide and/or transmit charging and/or powering energy; and
   a single receiver for receiving communication signals and energy, wherein the single receiver has and/or is configured to be switched into a first status for receiving communication signals of a communication transmission provided by the communication module and wherein the single receiver has and/or is configured to be switched into a second status for receiving charging energy of a charging transmission provided by the charging module, wherein the communication transmission and the charging transmission are separate transmissions received by the single receiver, wherein the single receiver comprises a single antenna and a communication and charging diplexer that form a tank circuit, wherein the tank circuit includes a capacitor that is positioned between the single antenna and a switch.

2. The system according to claim 1, wherein the first status and the second status are enabled at the same time.

3. The system according to claim 1, wherein the first status and the second status are alternating and/or are not enabled at the same time.

4. The system according to claim 1, wherein the communication transmitter is configured and arranged to transmit and send communication signals within a first frequency range and wherein the energy charging and/or energy transferring transmitter is configured and arranged to transmit and send charging energy within a second frequency range, the first and second frequency ranges being different from each other.

5. The system according to claim 1, wherein the single receiver is implantable or implanted into a subject and the communication module and/or the charging and/or powering module are not implanted into the subject.

6. The system according to claim 1, wherein each of the single receiver and the communication module and/or the charging and/or powering module is implantable or implanted into a subject.

7. The system according to claim 1, wherein at least one of the communication transmitter and the energy charging and/or energy transferring transmitter is/are embodied as an antenna or an antenna coil that utilizes magnetic induction.

8. The system according to claim 7, wherein the single antenna is an inductor and the communication and charging diplexer comprises the switch, the switch being a switch to ground, wherein the capacitor is a first capacitor, and wherein the first capacitor and a second capacitor are arranged in series and connected to the single antenna, and wherein the single antenna and the second capacitor form a resonant tank.

9. The system according to claim 8, wherein in a connection between the first capacitor and the second capacitor a branch-off line is connected, wherein the branch-off line is connected to a connection point, the connection point being a connection to a charging line and a communication line, and wherein in the communication line a third capacitor and a connection line to the switch to ground is arranged.

10. The system according to claim 9, wherein the third capacitor is arranged between the connection point and the connection line to the switch to ground.

11. The system according to claim 8, wherein in a connection line connecting the second capacitor and the single antenna a connection to ground is provided.

12. The system according to claim 7, wherein from the single antenna a branch-off line is connected, wherein the branch-off line is connected to a connection point, the connection point being connection to a charging line and a communication line, and wherein in the communication line a capacitor and a connection to the switch is arranged.

13. The system according to claim 1, wherein the switch is arranged between the capacitor and ground.

14. The system according to claim 7, wherein the single antenna is connected to the capacitor and a connection to ground, and wherein the capacitor and the connection to ground are arranged in series.

15. The system according to claim 1, wherein the single receiver is connected to a separate implantable medical device (IMD).

16. The system according to claim 15, wherein the IMD is an implantable pulse generator (IPG).

17. The system according to claim 15, wherein the IMD is rechargeable and/or is configured to be supplied with power/energy via the single receiver using the charging and/or powering module, and wherein, via the single receiver, communication signals are exchanged between the IMD and the communication module.

18. The system according to claim 1, wherein the communication and charging diplexer receives communication signals and charging energy.

19. A medical communication and powering system comprising:
   at least one communication module comprising a communication transmitter configured and arranged to transmit and send communication signals for a communication transmission;
   at least one charging and/or powering module comprising an energy charging and/or energy transferring transmitter configured and arranged to provide and/or transmit charging and/or powering energy for a charging transmission;

a single receiver for receiving communication signals and energy of the communication transmission and of the charging transmission;

a control unit; and a memory device storing instructions executable by the control unit to:

switch the single receiver into a first status for receiving communication signals provided by the communication module, and switch the single receiver into a second status for receiving energy provided by the charging module, wherein the communication transmission and the charging transmission are separate transmissions received by the single receiver, wherein the single receiver comprises a single antenna and a communication and charging diplexer that form a tank circuit, wherein the tank circuit includes a capacitor that is positioned between the single antenna and a switch, wherein the switch is positioned between the capacitor and ground, and wherein the single receiver is further configured to function as a transceiver that transmits and sends signals to the at least one communication module.

20. A method for a communication and powering system including a first part having a communication module, a charging and/or powering module, and a single receiver, the method comprising:

opening a switch of the first part of the communication and powering system to control the communication module to transmit communication signals as part of a communication transmission transcutaneously to a single antenna of the single receiver of the communication and powering system; and closing the switch of the first part to control the charging and/or powering module to transmit charging energy as part of a charging transmission to the single antenna of the single receiver, wherein the single receiver comprises a communication and charging diplexer, wherein the single antenna and the communication and charging diplexer form a tank circuit, and wherein the tank circuit includes a capacitor that is positioned between the single antenna and the switch.

* * * * *